United States Patent [19]
Antoniades et al.

[11] Patent Number: 4,861,757
[45] Date of Patent: Aug. 29, 1989

[54] WOUND HEALING AND BONE REGENERATION USING PDGF AND IGF-I

[75] Inventors: Harry N. Antoniades, Newton; Samuel E. Lynch, Jamaica Plain; Ray C. Williams, Arlington, all of Mass.

[73] Assignees: Institute of Molecular Biology, Boston; President and Fellows of Harvard College, Cambridge, both of Mass.

[21] Appl. No.: 120,943

[22] Filed: Nov. 16, 1987

Related U.S. Application Data

[63] Continuation-in-part of Ser. No. 930,762, Nov. 14, 1986.

[51] Int. Cl.⁴ .............................................. A61K 37/36
[52] U.S. Cl. ........................................ 514/21; 514/2; 514/3; 514/12; 424/101
[58] Field of Search ........................... 514/2, 3, 21, 12; 424/101

[56] References Cited

U.S. PATENT DOCUMENTS

| 4,085,204 | 4/1978 | Wacker et al. | 514/21 X |
| 4,350,687 | 9/1982 | Lipton et al. | 514/21 X |
| 4,479,896 | 10/1984 | Antoniades | 424/101 X |
| 4,604,234 | 8/1986 | Fujii et al. | 514/2 |
| 4,738,921 | 4/1988 | Belagaje et al. | 435/68 |
| 4,745,179 | 5/1988 | Ueda et al. | 530/303 |

OTHER PUBLICATIONS

Endocrinology, 118–124, 111: No. 1, (1982), Tashjian et al.
J. Dermatol. Surg. Oncol. 11:6, (1985), Leitzel et al., 617–622.
Science, vol. 230, 327–330 (1985), Leal et al.
Proc. Natl. Acad. Sci. U.S.A., 77, No. 11, 6611–6615 (1980), Heldin et al.
Proc. Natl. Acad. Sci. U.S.A., 76, No. 3, 1279–1283 (1979), Stiles et al.
Grotendorst (1984), J. Trauma, 24, 549–552.
Grotendorst (1985), J. Clin. Invest 76(6), 2323–2329 (Dec. 1985).
Soft & Hard Tissue Repair, vol. 2 (1984), pp. 20–40, Grotendorst et al.
Chem Abstracts, vol. 102, 43765v, Michaeli et al, effective date 1984.
Michaeli et al. (1984) Soft and Hard Tissue Repair 380–394.
Computer printout of various patent abstracts.
Rinderknecht et al., Elsevier/North–Holland Biomedical Press, 89:283–286, (May, 1978).
KabiGen Commercial Literature.
Ernesto Canalis, Metabolism, vol. 30, No. 10, pp. 970–975 (Oct. 1981).

Primary Examiner—Howard E. Schain
Attorney, Agent, or Firm—Paul T. Clark

[57] ABSTRACT

Healing an external wound or regenerating bone of a mammal by administering to the mammal a composition containing purified platelet-derived growth factor and purified insulin-like growth factor.

9 Claims, No Drawings

WOUND HEALING AND BONE REGENERATION USING PDGF AND IGF-I

BACKGROUND OF THE INVENTION

This application is a continuation-in-part of Antoniades et al., entitled "Healing External Wounds," U.S. Ser. No. 930,762, filed Nov. 14, 1986, hereby incorporated by reference, now abandoned.

This invention relates to healing wounds.

Growth factors are polypeptide hormones which stimulate a defined population of target cells. Examples of growth factors include platelet-derived growth factor (PDGF), insulin-like growth factor (IGF-I), transforming growth factor beta (TGF-$\beta$), epidermal growth factor (EGF), and fibroblast growth factor (FGF). PDGF is a cationic, heat-stable protein found in the granules of circulating platelets which is known to stimulate in vitro protein synthesis and collagen production by fibroblasts. It is also known to act as an in vitro mitogen and chemotactic agent for fibroblasts, smooth muscle cells, and glial cells.

It has been proposed to use PDGF to promote in vivo wound healing. For example, Grotendorst (1984) J. Trauma 24:549-52 describes adding PDGF to Hunt-Schilling wire mesh chambers impregnated with a collagen gel and implanted in the backs of rats; PDGF was found to increase the amount of new collagen synthesized. However, Leitzel et al. (1985) J. Dermatol. Surg. Oncol. 11:617-22 were unable to accelerate normal wound healing in hamsters using PDGF alone or in combination with FGF and EGF.

Michaeli, et al. (1984) In *Soft and Hard Tissue Repair*(Hunt, T. K. et al., Eds), Praeger Publishers, New York, pp. 380-394, report that application of a partially purified preparation of PDGF obtained from platelet-rich plasma stimulated angiogenesis when implanted in rabbit corneas. Because PDGF is not an angiogenic growth factor the investigators suggested that an unknown factor in their partially purified PDGF preparation was responsible for the angiogenic effect.

SUMMARY OF THE INVENTION

In general, the invention features, in one aspect, healing an external wound in a mammal, e.g., a human patient, by applying to the wound an effective amount of a composition that includes purified PDGF and purified IGF-I. The composition aids in healing the wound, at least in part, by promoting the growth of epithelial and connective tissue and the synthesis of total protein and collagen. Wound healing using the composition of the invention is more effective than that achieved in the absence of treatment (i.e., without applying exogenous agents) or by treatment with purified PDGF alone, or purified IGF-I alone.

In another aspect, the invention features regenerating bone of a mammal, e.g., a human patient, by administering to the patient, preferably by application to the area of injured or depleted bone, an effective amount of a composition that includes purified PDGF and purified IGF-I. The composition aids in regeneration, at least in part, by promoting the growth of connective tissue, bone, and cementum, and by stimulating protein and collagen synthesis. Regeneration using the composition of the invention is more effective than that achieved in the absence of treatment (i.e., without applying exogenous agents) or by treatment with purified PDGF alone, or purified IGF-I alone.

In preferred embodiments of both aspects of the invention, the composition is prepared by combining, in a pharmaceutically acceptable carrier substance, e.g., commercially available inert gels or liquids (e.g., saline supplemented with albumin or methyl cellulose), purified PDGF and IGF-I (both of which are commercially available). Most preferably purified PDGF and IGF-I are combined in a weight-to-weight ratio of between 1:4 and 25:1, preferably between 1:2 and 10:1, and more preferably 1:1 or 2:1. The purified PDGF and IGF-I may be obtained from human platelets or by recombinant DNA technology. Thus, by the terms "PDGF" and "IGF-I" we mean both platelet-derived and recombinant materials of mammalian, preferably primate, origin; most preferably, the primate is a human, but can also be a chimpanzee or other primate. Recombinant PDGF can be recombinant heterodimer, made by inserting into cultured prokaryotic or eukaryotic cells DNA sequences encoding both subunits, and then allowing the translated subunits to be processed by the cells to form heterodimer, of DNA encoding just one of the subunits (preferably the beta or "2" chain) can be inserted into cells, which then are cultured to produce homodimeric PDGF (PDGF-1 or PDGF-2 homodimer).

The term "purified" as used herein refers to PDGF or IGF-I which, prior to mixing with the other, is 95% or greater, by weight, PDGF or IGF-I, i.e., is substantially free of other proteins, lipids, and carbohydrates with which it is naturally associated.

A purified protein preparation will generally yield a single major band on a polyacrylamide gel for each subunit of PDGF or IGF-I. Most preferably, the purified PDGF or IGF-I used in the compositions of the invention is pure as judged by amino-terminal amino acid sequence analysis.

The composition of the invention provides a fast, effective method for healing external wounds of mammals, e.g., bed sores, lacerations and burns. The composition enhances connective tissue formation compared to natural healing (i.e. no exogenous agents added) or pure PDGF or IGF-I alone. Unlike pure PDGF alone, the composition promotes about a 250% increase in new connective tissue and about a 95% increase in the growth of epithelial tissue. The epithelial layer obtained is thicker than that created by natural healing, and also contains more epithelial projections connecting it to the new connective tissue; it is thus more firmly bound and protective. In addition, scar formation is minimized.

The composition of the invention also provides a fast, effective method for regeneration of connective tissue and bone of mammals, e.g., humans, with a history of peridontal disease. The composition enhances connective tissue and bone formation compared to natural healing (i.e. no exogenous agents added) or pure PDGF or IGF-I alone.

Other features and advantages of the invention will be apparent from the following description of the preferred embodiments thereof, and from the claims.

Description of the Preferred Embodiments

We now describe preferred embodiments of the invention.

External wounds, e.g., bed sores and burns, are treated, and bone and connective tissue regenerated, according to the invention, with PDGF/IGF-I mixtures prepared by combining pure PDGF and IGF-I. IGF-I is commercially available from Amgen Corporation (Thousand Oaks, CA) and Kabi (Sweden). Purified recombinant PDGF and purified PDGF derived from human platelets are commercially available from PDGF, Inc. (Boston, MA), collaborative Research (Waltham, MA), and Amgen Corp. (Thousand Oaks, CA). Purified PDGF can also be prepared as follows:

Five hundred to 1000 units of washed human platelet pellets are suspended in 1M NaCl (2 ml per platelet unit) and heated at 100° C. for 15 minutes. The supernatant is then separated by centrifugation and the precipitate extracted twice with the 1M NaCl.

The extracts are combined and dialyzed against 0.08M NaCl–0.01M sodium phosphate buffer (pH 7.4) and mixed overnight at 4° C. with CM-Sephadex C-50 equilibrated with the buffer. The mixture is then poured into a column (5×100 cm), washed extensively with 0.08M NaCl–0.01M sodium phosphate buffer (pH 7.4), and eluted with 1M NaCl while 10 ml fractions are collected.

Active fractions are pooled and dialyzed against 0.3M NaCl–0.01M sodium phosphate buffer (pH 7.4), centrifuged, and passed at 4° C. through a 2.5×25 cm column of Blue Sepharose (Pharmacia) equilibrated with 0.3M NaCl–0.01M sodium phosphate buffer (pH 7.4). The column is then washed with the buffer and partially purified PDGF eluted with a 1:1 solution of 1M NaCl and ethylene glycol.

The partially purified PDGF fractions are diluted (1:1) with 1M NaCl, dialyzed against 1M acetic acid, and lyophilized. The lyophilized samples are dissolved in 0.8M NaCl–0.1M sodium phosphate buffer (pH 7.4) and passed through a 1.2×40 cm column of CM-Sephadex C-50 equilibrated with the buffer. PDGF is then eluted with a NaCl gradient (0.08 to 1M).

The active fractions are combined, dialyzed against 1M acetic acid, lyophilized, and dissolved in a small volume of 1M acetic acid. 0.5 ml portions are applied to a 1.2×100 cm column of Biogel P-150 (100 to 200 mesh) equilibrated with 1 M acetic acid. The PDGF is then eluted with 1M acetic acid while 2 ml fractions are collected.

Each active fraction containing 100 to 200 mg of protein is lyophilized, dissolved in 100 ml of 0.4% trifluoroacetic acid, and subjected to reverse phase high performance liquid chromatography on a phenyl Bondapak column (Waters). Elution with a linear acetonitrile gradient (0 to 60%) yields pure PDGF.

PDGF made by recombinant DNA technology can be prepared as follows:

Patelet-derived growth factor (PDGF) derived from human platelets contains two polypeptide sequences (PDGF-1 and PDGF-2 polypeptides; Antoniades, H. N. and Hunkapiller, M. (1983) Science 220:963–965). PDGF-1 is encoded by a gene localized in chromosome 7 (Betsholtz, C. et al., Nature 320:695–699), and PDGF-2 is encoded by the sis oncogene (Doolittle, R. et al. (1983) Science 221:275–277) localized in chromosome 22 (Dalla-Favera, R. (1982) Science 218:686–688). The sis gene encodes the transforming protein of the Simian Sarcoma Virus (SSV) which is closely related to PDGF-2 polypeptide. The human cellular c-sis also encodes the PDGF-2 chain (Rao, C. D. et al. (1986) Proc. Natl. Acad. Sci. USA 83:2392–2396). Because the two polypeptide chains of PDGF are coded by two different genes localized in separate chromosomes, the possibility exists that human PDGF consists of a disulfide-linked heterodimer of PDGF-1 and PDGF2, or a mixture of the two homodimers (homodimer of PDGF-1 and homodimer of PDGF-2), or a mixture of the heterodimer and the two homodimers.

Mammalian cells in culture infected with the Simian Sarcoma Virus, which contains the gene encoding the PDGF-2 chain, were shown to synthesize the PDGF-2 polypeptide and to process it into a disulfide-linked homodimer (Robbins, K. et al. (1983) Nature 305:605–608). In addition, PDGF-2 homodimer reacts with antisera raised against human PDGF. Furthermore, the functional properties of the secreted PDGF-2 homodimer are similar to those of platelet-derived PDGF in that it stimulates DNA synthesis in cultured fibroblasts, it induces phosphorylation at the tyrosine residue of a 185 kd cell membrane protein, and it is capable of competing with human ($^{125}$I)-PDGF for binding to specific cell surface PDGF receptors (Owen, A. et al. (1984) Science 225:54–56). Similar properties were shown for the sis/PDGF-2 gene product derived from cultured normal human cells (for example, human arterial endothelial cells), or from human malignant cells expressing the sis/PDGF-2 gene (Antoniades, H. et al. (1985) Cancer Cells 3:145–151).

The recombinant PDGF-2 homodimer is obtained by the introduction of cDNA clones of c-sis/PDGF-2 gene into mouse cells using an expression vector. The c-sis/PDGF-2 clone used for the expression was obtained from normal human cultured endothelial cells (Collins, T., et al. (1985) Nature 216:748–750).

Wound Healing

To determine the effectiveness of PDGF/IGF-I mixtures in promoting wound healing, the following experiments were performed.

Young white Yorkshire pigs (Parson's Farm, Hadley, MA) weighing between 10 and 15 kg were fasted for at least 6 hours prior to surgery and then anesthetized. Under aseptic conditions, the back and thoracic areas were clipped, shaved, and washed with mild soap and water. The area to be wounded was then disinfected with 70% alcohol.

Wounds measuring 1 cm×2 cm were induced at a depth of 0.5 mm using a modified Castroviejo electrokeratome (Storz, St. Louis, MO, as modified by Brownells, Inc.). The wounds resulted in complete removal of the epithelium, as well as a portion of the underlying dermis (comparable to a second degree burn injury). Individual wounds were separated by at least 15 mm of unwounded skin. Wounds receiving identical treatment were organized as a group and separated from other groups by at least 3 cm. Wounds receiving no growth factor treatment were separated from wounds receiving such treatment by at least 10 cm.

The wounds were treated directly with a single application of the following growth factors suspended in biocompatible gel: 1) 500 ng pure human PDGF (purified by high performance liquid chromatography) or recombinant PDGF alone; 2) 500 ng pure PDGF in combination with each of the following: a) 500 ng EGF; b) 500 ng EGF plus 500 ng IGF-I; c) 500 ng IGF-I.

Following wounding, biopsy specimens were taken on days 3 through 10. Biopsy specimens for histologic evaluation were taken as wedges approximately 3 mm deep and placed in 10% formalin. Specimens for biochemical analysis and autoradiography were obtained using an electrokeratome. The final dimensions of the specimens were 1.5 mm×10 mm×1.5 mm. Three specimens per wound were collected for biochemical analysis, while two specimens per wound collected for autoradiography. Following collection, the specimens were stored in cold Eagle's Modified Essential Medium (EMEM) media supplemented with 10% fetal calf serum. The biopsy specimens were analyzed as follows.

Autoradiography

Biopsy specimens were incubated in 0.3 ml Eagle's Modified Essential Medium (EMEM) plus 10% fetal calf serum containing 15 $\mu$Ci/ml of $^3$H-thymidine for one hour; the specimens were then washed twice with 10% formalin. Four micron sections were made from the specimens using standard paraffin impregnating and embedding techniques. They were then deparaffinized, dipped in Nuclear Tract emulsion NTB-2 (Kodak), and exposed for two weeks. Subsequently, they were developed and stained with hematoxylin and eosin.

Autoradiograms of the stained specimens were recorded and scored at equally distributed points by counting the total number of labelled cells (5 grains or more per cell) versus the total number of cells in the area.

Histologic Evaluation

Histologic specimens were prepared using standard paraffin impregnating and embedding techniques. Four micron sections were made and stained using filtered Harris hemotoxylin and alcoholic eosin; they were then observed under a microscope. All specimens were scored blindly by two investigators at equally distributed points throughout the sections. The widths of the epithelial and connective tissue layers were scored using a grid placed within the ocular of the microscope; the measurement was then converted into millimeters using a micrometer viewed under the same conditions.

In Vitro Metabolic Labelling

Biopsy specimens were transferred to individual tubes containing 0.3 ml of EMEM plus 10% fetal calf serum, 15 $\mu$Ci/ml $^3$H-thymidine, and 5 $\mu$Ci/ml $^{14}$C-leucine, and incubated for one hour at 37° C. At the end of the hour, the medium was removed and tissue metabolism stopped by adding 0.5 ml cold 5% perchloric acid. The specimens were then finely minced and washed three times; the resulting precipitate was resuspended in 0.5 ml 14.8M ammonium hydroxide and sonicated. Following sonication, the specimens were incubated in sealed tubes at 45° C. for 16-24 hours, resonicated, and the radioactivity measured using standard liquid scintillation methods with cross channel counting.

DNA and Protein Determination

DNA determination was performed using a modification of the method of Labarca et al. (1980) Anal. Biochem. 120:344-52. A 50 $\mu$l aliquot of tissue extract in concentrated ammonium hydroxide was added to 400 $\mu$l of a buffer solution containing 1M sodium phosphate and 2M sodium chloride (pH 7.0); the pH of the resulting solution was adjusted to 7.4 using HCl. Afterwards, the final solution volume was brought to 500 $\mu$l, while maintaining the pH at 7.4. The solution was then added to 2.5 ml of a buffered solution (0.05M sodium phosphate, 2M sodium chloride, pH=7.4) of Hoesht dye (1.14 mg/ml). Fluorescence was induced at an excitation wavelength of 352 nm and emission measured at 454 nm. Calf thymus DNA prepared by identical treatment was used to develop standard curves.

Protein content of the tissue extract in concentrated ammonium hydroxide was measured by the bradford method (Bradford (1976) Anal. Biochem. 72:248-54), with bovine serum albumin as a standard.

Results

The results from histologic evaluation indicated that wounds treated with the combination of purified human PDGF or recombinant PDGF and IGF-I had thicker connective tissue and epithelial layers, and more extensive epithelial projections connecting these layers, than wounds receiving no treatment, pure IGF-I, pure PDGF, or PDGF in combination with other growth factors. There was no evidence of scar formation upto 6 weeks following treatment. Autoradiography revealed an increase in the percentage of $^3$H-thymidine-labelled cells in PDGF/IGF-I-treated wounds than wounds receiving no treatment, PDGF alone, or IGF-I alone. Metabolic labelling results showed that the uptake of $^3$H-thymidine and $^{14}$C-leucine was greater for wounds treated with purified PDGF/IGF-I preparations than for wounds receiving no treatment; the PDGF/IGF-I-treated wounds similarly had greater DNA and protein contents.

The recombinant purified PDGF-2 homodimer, prepared as described above, was also tested in partial thickness skin wounds alone and in combination with IGF-I. Histological analysis of the six day old wounds indicate that the application of PDGF-2 or IGF-I alone resulted in no significant differences from controls in connective tissue or epidermal morphology. However, when PDGF-2 was combined with IGF-I, the combination produced a 2.0 fold increase in the width of the new connective tissue layer and a 20% increase in epidermal thickness at six days postoperatively. At nine days PDGF-2 alone resulted in a 22% increase in both new connective tissue and epidermal thickness. PDGF-2 in combination with IGF-I resulted in 75% increases in both the new connective tissue and epidermal layers. The connective tissue of PDGF-2/IGF-I treated wounds had definite areas of polarization of light indicating these wounds contained more mature connective tissue than either wounds receiving PDGF-2 alone or no treatment.

Thus, application of recombinant PDGF-2 to wound healing using the animal model described above, produces results similar to those with purified human PDGF when combined with recombinant IGF-I. The combination of recombinant PDGF-2 and IGF-I produces dramatic increases in the number of new fibroblasts and the rate of collagen synthesis, accompanied by hyperplasia of the dermis and epidermis (2.5-fold total increase) compared to the control animal in the absence of treatment or by treatment with recombinant PDGF-2 or IGF-I alone.

These results indicate that recombinant PDGF-2 homodimer and native purified human PDGF both interact synergistically with IGF-I when applied topically to wounds.

Dosage

To determine the appropriate dosage of purified PDGF, the above-described experiments were repeated except that the wounds were treated with 2.5 ng, 5.0 ng, and 10 ng PDGF equivalents of purified PDGF per square millimeter of wound dispersed in 30 $\mu$l of biocompatible gel. The results showed that optimum effects were produced when the PDGF content was 5.0 ng/mm$^2$ or higher.

To determine the appropriate dosage of pure PDGF plus IGF-I, combinations in which the weight to weight ratio of PDGF to IGF-I ranged from 1:10 to 25:1 were evaluated as described above. Optimum results were achieved with a ratio of between 1:1 and 2:1.

Bone Regeneration

To determine the effectiveness of PDGF/IGF-I preparations in promoting periodontium and/or bone growth, the following experimentws were performed.

Beagle dogs with naturally occurring periodontal disease were selected on the basis of an initial radiographic examination. The teeth which exhibited 30% to 80% bone loss were initially scaled using ultrasonic instruments. Surgical flaps and root planing techniques were then performed, and the experimental teeth were treated with a composition containing purified PDGF and IGF-I in a pharmaceutically acceptable carrier substance, e.g., commercially available inert gels, e.g., methyl cellulose. Teeth in the remaining quadrants received control gel alone, or pure PDGF or IGF-I alone. Block biopsies of the teeth and bone were taken at two weeks postsurgery and prepared for histologic evaluation using standard demineralizing and processing techniques.

Results

Results of histologic analysis of periodontal and bone specimens indicated that, adjacent to the root surfaces of experimental specimens (i.e., those treated with the PDGF/IGF-I combination), distinct areas of new bone formation were present and a deposit resembling cementum was present on the root surface adjacent to the new bone. New bone was also present on the periosteal surface of the specimens, and areas of ankylosis had occurred within the apical extent of the ligament. A dense layer of osteoblast-like cells, and connective tissue lined the newly formed bone with newly formed collagen fibers inserting into the newly formed cementum.

In the control specimens there was no evidence of new bone formation, an absence of new cementum-like deposits, and connective tissue was oriented perpendicular to the bony surface appearing to form a "cap" over the original bone. The results thus indicate that the PDGF/IGF-I composition of the invention enhances osteogenic and connective tissue responses.

Other embodiments are within the following claims.

We claim:

1. A method for healing an external wound of a mammal comprising applying to said wound a wound-healing amount of a composition comprising platelet-derived growth factor and insulin-like growth factor-1, each said platelet-derived growth factor and insulin-like growth factor-1 being pure so as to yield a single major band on a polyacrylamide gel.

2. A method for regenerating bone of a mammal comprising administering to said mammal a wound-healing amount of a composition comprising platelet-derived growth factor and insulin-like growth factor-1, each said platelet-derived growth and insulin-like growth factor-1 being pure so as to yield a single major band on a polyacrylamide gel.

3. The method of claim 1 or claim 2 wherein the weight to weight ratio of said platelet-derived growth factor to said insulin-like growth factor-1 in said composition is between 1:4 and 25:1.

4. The method of claim 3 wherein said ratio is between 1:2 and 10:1.

5. The method of claim 4 wherein said ratio is between about 1:1 and 2:1.

6. A wound healing and bone regenerating composition comprising platelet-derived growth factor and insulin-like growth factor-1, in a weight to weight ratio of 1:4 to 25:1, each said platelet-derived growth factor and insulin-like growth factor-1 being pure so as to yield a single major band on a polyacrylamide gel, in combination with a pharmaceutically acceptable carrier substance.

7. The composition of claim 6 wherein said ratio is between 1:2 and 10:1.

8. The composition of claim 7 wherein said ratio is between about 1:1 and 2:1.

9. A method for preparing a composition for healing wounds, comprising mixing platelet-derived growth factor and insulin-like growth factor-1 in a weight to weight ratio of between 1:4 and 25:1, in combination with a pharmaceutically acceptable carrier substance, each said platelet-derived growth factor and insulin-like growth factor-1 being pure so as to yield a single major band on a polyacrylamide gel.

* * * * *